United States Patent [19]
Riera et al.

[11] Patent Number: 6,159,352
[45] Date of Patent: Dec. 12, 2000

[54] PROCESS FOR THE ELECTROCHEMICAL SYNTHESIS OF N-ACETYLCYSTEINE FROM CYSTINE

[75] Inventors: Antonio Aldaz Riera, Campello; Vicente Montiel Leguey, Santa Pola; Vicente Garcia Garcia, Torrevieja; José Gonzalez Garcia, Elche, all of Spain

[73] Assignee: Universidad de Alicante, Alicante, Spain

[21] Appl. No.: 09/180,385

[22] PCT Filed: May 7, 1997

[86] PCT No.: PCT/ES97/00113

§ 371 Date: Jan. 12, 1999

§ 102(e) Date: Jan. 12, 1999

[87] PCT Pub. No.: WO97/42358

PCT Pub. Date: Nov. 13, 1997

[30] Foreign Application Priority Data

May 7, 1996 [ES] Spain ................................ 9601014

[51] Int. Cl.[7] .................................................... C25B 3/04
[52] U.S. Cl. ........................ 204/530; 204/541; 205/435
[58] Field of Search ............................. 204/530, 541; 514/562; 205/435

[56] References Cited

FOREIGN PATENT DOCUMENTS

| | | |
|---|---|---|
| 436055 | 7/1991 | European Pat. Off. . |
| 2577242 | 8/1986 | France . |
| 2032155 | 1/1993 | Spain . |
| 1030259 | 5/1966 | United Kingdom . |
| WO 96 38601 | 12/1996 | WIPO . |

OTHER PUBLICATIONS

Patent Abstract of Japan, 1988, 12:358 & JP 63 112546 no month available.
Patent Abstract of Japan, 1977, 1:45 & JP 52003021 no month available.

*Primary Examiner*—Arun S. Phasge
*Attorney, Agent, or Firm*—Klauber & Jackson

[57] ABSTRACT

The process comprises: (A) obtainment of N-acetyl-cysteine from L-cystine, by means of the following steps:
 (i) acetylation of L-cystine to produce N-acetyl-cystine;
 (ii) electroreduction and desalination by electrodialysis of the N-acetyl-cystine thus produced to give N-acetyl-cysteine; or (B) obtainment of N-acetyl-cysteine from L-cystine, by means of the following steps:
 (i) acetylation and desalination of L-cystine to produce N-acetyl-cystine;
 (ii) electroreduction of N-acetyl-cystine which may or may not come from the preceding step (i) to produce N-acetyl-cysteine; (C) obtainment of N-acetyl-cysteine from L-cystine by means of the following steps:
 (i) electroreduction of L-cystine to produce L-cysteine;
 (ii) acetylation and desalination by electrodialysis of L-cysteine, which may or may not come from the preceding step (i) to produce N-acetyl-cysteine.

The N-acetyl-cysteine thus obtained has important uses in the pharmaceutical sector.

32 Claims, 2 Drawing Sheets

PROCESS FOR THE ELECTROCHEMICAL SYNTHESIS OF N-ACETYLCYSTEINE FROM CYSTINE

This application is a 371 of PCT/ES97/00113 filed on May 7, 1997.

TECHNICAL FIELD OF THE INVENTION

The present invention is within the technical field of processes for producing N-acetyl-cysteine, which is a product with important applications in the pharmaceutical sector.

More specifically, the present invention provides a new process for the electrochemical synthesis of N-acetyl-cysteine which has clear advantages over conventional processes, especially, as far as the quality of the product is concerned, as well as the environmental impact.

PRIOR ART OF THE INVENTION

N-acyl-cysteine derivatives, in which the acyl group can come from a mono or dicarboxylic acid and, in particular, monoacyl derivatives among which is N-acetyl-cysteine, have therapeutic applications as a mucolytic (U.S. Pat. No. 3,184,505 (1965)), in the treatment of cornea lesions (Bull. Mem. Soc. Fr. Ophthalmol. 94,425 (1982)), as an antidote in aminoketophen overdose (Review Pharmacological and Biochemical Properties of Drug Substances, vol. 2. M. E. Goldberg Ed. (An. Pharm. Assoc. Washington, D.C., 1979), pp. 479–488).

More recently, its use in the prevention of apoptotic death of neuron cells has been described (Journal of Neuroscience, 15, 4, (1995)), the inhibition by N-acetyl-cysteine of the interleucine 6 RNA messenger (Febbs Letter. 353, 1 (1994)), the suppression of antiproliferous effects of the tumoral necrosis factor (ibid.), and the regulation of nitric acid cytochina synthetase in rat retina pigments (Experimental Eye Research. 59, 2 (1994)).

N-acetyl-L-cysteine of formula (I)

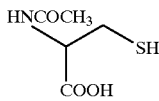

(I)

is obtained conventionally by monoacetylation of L-cysteine hydrochloride of formula (II):

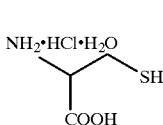

(II)

in a suitable aqueous-organic solvent. The nature of this solvent makes the yield of the reaction vary between 60 and 95%. However, compound (II) is not a raw material available commercially, but rather it must be obtained by reduction of L-cystine of formula (III):

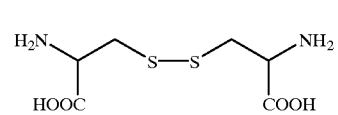

(III)

either using conventional reducing agents or using electrochemical reduction.

In this process, separation of (I) from the solution coming from acetylation of (II) implies handling solutions with very high salt contents in acetate that may influence the quality of the product, if its application is centered within the pharmaceutical field. On the other hand, in order to obtain (I) from (II) it is necessary that the latter product (II) is perfectly separated from product (III) used as a starting material in the synthesis thereof since traces of (III) could harm the following step of the process.

On the other hand, there is the possibility of obtaining N-acetyl-L-cysteine (I) by reduction of bis-acetyl-L-cystine of formula (IV):

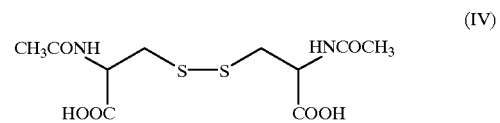

(IV)

by means of using conventional reducing agents such as zinc. In turn, compound (IV) would be obtained previously by acetylation of (III).

The problem of this second alternative process mainly lies on the reduction phase. When the reducing agent, normally metallic zinc, has acted it converts into $Zn^{+2}$, whereby the desired compound (I) must be isolated in a medium that has a high salt content in $Zn^{+2}$ which involves problems of separation and of quality of the obtained final product. On the other hand, residual water, that has a high salt content in $Zn^{+2}$ ions, constitutes an important environmental problem.

Another aspect of this reduction to be considered is that significant volumes of hydrogen gas are produced which, as known, is a dangerous gas to handle due to its potential explosion capacity.

On the other hand, the excess of unconverted zinc metal has to be eliminated by forming the corresponding lead mercaptan, followed by isolation, treatment with hydrogen sulfide, elimination of the lead sulfide formed, lyophilization of the solution and subsequent recrystallizations with solvents, in order to achieve a final yield of approximately 48% (M. W. Pirie et al. Biochemical Journal 2, 614 (1931); M. W. Pirle et al. Ibid., 27, 1716 (1933); Smith, Gorin. J. Org. Chem. 26, (1961); and Greenstein. Chemistry of the Amino Acids. Vol. 3. Ed Krieger. Florida (1984).

U.S. Pat. No. 3,184,505 describes a selective monoacetylation process starting with cysteine hydrochloride, since acetylation thereof normally leads to N,S-diacyl compounds. The process is carried out by suspending or dissolving cysteine in a buffer and in a suitable solvent. Due to the problems of decomposition of cysteine in a basic medium and at temperatures higher than 20° C., the use of refrigeration systems and the use of an inert atmosphere (nitrogen, helium . . . ) are necessary. The N-acetyl-L-cysteine salt formed is much stabler than cysteine itself in that medium.

Due to the need of a solvent in the initial stage of the process, it is necessary to use complex and costly equipment, as well as to previously neutralize the hydrochloride and to eliminate the salt content before isolation of the product.

Therefore, it is still necessary to achieve a process that eliminates or reduces the problems of the classic processes for the obtainment of N-acetyl-L-cysteine.

For this purpose the present invention has been developed and completed, wherein it provides a new process for the electrochemical synthesis of N-acetyl-cysteine with important advantages over the processes of the prior art.

DETAILED DESCRIPTION OF THE INVENTION

Just as it is indicated in the title, the present invention refers to a new process for the electrochemical synthesis of N-acetyl-cysteine from cystine.

The process of the present invention comprises a first phase of acetylation of the cystine of formula (III):

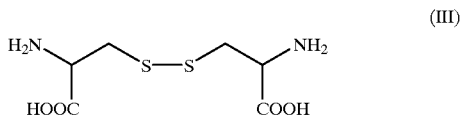

in an aqueous solution and with acetic anhydride. Any of the usual processes described in the bibliography is used for this phase. For example, (III) is dissolved in an aqueous solution of an alkali metal or alkaline earth metal hydroxide, preferably sodium hydroxide, with a pH higher than 7 and at a temperature of about 0° C.

After this acetylation step has ended, a reaction solution will be obtained containing the bis-acetyl-L-cystine (IV) produced, alkali metal or alkaline earth metal acetate, preferably sodium acetate, and water.

This solution is subjected to electrochemical treatment of desalination and reduction which can be carried out sequentially or simultaneously, said electrochemical treatment constituting the object of the present invention.

In the first alternative, the solution containing (IV) is first subjected to a desalination process by means of the use of conventional reverse or cascade electrodialysis, in order to obtain a solution that will have lost most of its salt content (alkaline or alkaline earth acetate). This solution is then subjected to an electrochemical reduction process. After said process has ended, a solution (I) with a low salt content, which can be optimally treated to isolate the desired product (I), with a quality capable of meeting the requirements of U.S. Pharmacopoeia, is obtained.

In the second alternative, the solution containing (IV) is subjected to a simultaneous electrochemical desalination and reduction process with a suitable electrochemical reactor. A solution containing (I) with a low salt content which, as before, can be treated optimally to separate the desired product with the required quality, is obtained with it in a single electrochemical step.

Each one of the two alternatives of the process of the present invention is explained hereinafter in more detail.

In the first alternative, the solution resulting from the acetylation of (III), containing (IV), is subjected to a conventional reverse or cascade electrodialysis process, as shown in FIG. 1.

The solution is fed in the compartment labeled solution to be diluted, while as the solution to be concentrated an aqueous solution of sodium acetate will be used. The anode reaction and cathode reaction will be formed by the same or different dissociated acid or base salt solutions. A flat or three-dimensional electrode made out of a material selected from among the following list: metals, conductor oxides or carbonous compund or graphite derivatives, a gas diffusion cathode, is used as a cathode. A stable electrode selected from among: Ti-Pt, Ti-Pb, DSA oxygen, DSA chlorine, $PbO_2$, vitreous carbons, gas diffusion anode, will be used as the anode. The cathode and anode would not be restrictive of the invention. The membranes used for electrodialysis will be an assembly of anionic and cationic membranes chosen from among: NAFION, NEOSEPTA, ASAHI, AQUALYTIC or any other commercial one. In order to make the system function current densities between 1 and 1000 $mA/cm^2$ will be established, the current density being able to be constant or variable with time. After having finished the electrodialysis process a concentrated solution that has increased its content of alkali metal or alkaline earth metal acetate is obtained and a diluted solution that contains IV and in which the content of said acetate has noticeably reduced is obtained. As well known in the art, the abbreviation "DSA" as used above and hereinafter, means Dimensional Stable Anode.

The electrodialysis operation can be carried out with the following composition of solutions:

Solution to be Diluted Compartment

An alkali or alkaline earth cation acetate whose concentration interval which can vary between 0.01 M and the maximum concentration that permits its solubility in this medium, and by N-acetyl-cystine in a concentration interval of 0.01 to 4 M. The pH can vary between 2.5 and 10.

Solution to be Concentrated Compartment

Any salt solution, preferably an alkali or alkaline earth cation acetate whose concentration interval can vary between 0.01 M and the maximum concentration that permits its solubility in this medium. Preferably, the acetate is sodium acetate and its concentration is comprised between 0.01 and 20 M.

Subsequently the solution that contains IV called diluted solution is subjected to an electroreduction process in a reactor or electrochemical cell or electrosynthesis cell that will be formed by, at least, one cathode and one anode, one catholyte and one anolyte separated by some suitable separation means, such as a ionic exchange membrane or any other suitable separator.

Electrodes constituted by graphite, carbon or derivatives thereof, lead, tin, zinc, copper, platinized titanium, any other steel or alloy in which iron, aluminum, or alloys thereof with gallium, indium or thallium, gas diffusion cathodes intervene, or preferably, a three-dimensional electrode of graphite, carbon or derivatives thereof with a suitable current collector can be used as a cathode. A stable electrode selected from among: Ti-Pt, Ti-Pb, DSA oxygen, DSA chlorine, $PbO_2$, vitreous carbon, graphite, a gas diffusion anode, is used as an anode, without these electrodes being restrictive of the invention. However, so that the yields and selectivity are adequate and in order to prevent contamination by heavy metals in the final product, as lead has to be used, it is preferable to use one or several cathodes constituted by a lead electrode, since the nature and shape of the electrode decisively influences the quality of the final product. Likewise, the required pharmaceutical quality implies that the electrosynthesis cell includes one or several anodes constituted by DSA-oxygen, for the purpose of preventing the problems of corrosion detected in other types of anodes used and that would lead to a product of non-pharmaceutical quality (US Pharmacopoeia).

The catholyte, or solution in contact with the cathode will be formed by the solution coming from the ELECTRODI- ALYSIS (diluted solution) and that contains IV. The anolyte, or solution that is in contact with the anode, can be formed by an aqueous solution of any saline electrolyte, for example, an aqueous solution of sodium sulfate.

The catholyte and anolyte have to be necessarily separated by some suitable separating means, such as an ionic exchange membrane, preferably a selective membrane that permits the passing of cations but not of anions, or by any other type of separator. These membranes will be chosen from among the commercial ones, NAFTON, NEOSEPTA, SYBRON, LONICS, AQUALYTIC or any other commercial one.

Just as it has been indicated, the electrodes can be flat or can have any other shape or structure and may be arranged in a filter-press type cluster or the like. Preferably, three-dimensional electrodes must be used.

The connection of the electrodes to the source may be monopolar, bipolar or mixed, preferably, the bipolar one due to the specific design of the electrosynthesis cell. Electrolysis may be carried out at a temperature between 0 and 90° C.

The current density can be between 1 $mA/cm^2$ and 5000 mA/cm and it does not, necessarily, have to remain constant during electrolysis.

In one embodiment of the invention, the electroreduction operation is done with the composition of solutions: Catholyte: Alkali or alkaline earth cation acetate whose concentration interval can vary between 0.01 M and the maximum concentration that permits its solubility in this medium, and by N-acetyl-cystine in a concentration interval of 0.1 to 4 M. The pH can vary between 2.5 and 10. Anolyte: Aqueous solution of any saline electrolyte.

Preferably, the acetate is sodium acetate and its concentration can be between 0.01 M and 20 M.

Once the electrosynthesis is considered to be finished, the catholyte is subjected to a reduced pressure distillation process in which the water is eliminated. Then an alcohol, preferably, one of the following ones: ethanol, isopropanol, methanol, is added to the residue. A hydrochloric acid solution is added to the resulting solution until the pH reaches a value lower than 2. A white precipitate which is separated, will appear. The resulting solution is subjected to reduced pressure distillation until all the solvent is eliminated, remaining a solid which corresponds to the desired product (I). This white solid is crystallized and recrystallized in water obtaining a white solid that complies with the characteristics of the desired product so that it is used as a pharmaceutical product. These analytical characteristics are:

| | |
|---|---|
| HPLC richness | >98.2% |
| Specific rotation | +21 to +27 |
| Ignition residue | <0.5% |
| Heavy metals | <10 ppm |
| Loss by drying | <1.0% |
| Arsenic | <5 ppm |

In the second alternative, the solution resulting from the acetylation of (III), containing (IV) is subjected to a process of electrodialysis+electrochemical reduction coupled in an electrochemical reactor just as it is shown in FIG. 2.

The solution that contains IV (IV+Acetate in FIG. 2) is subjected to a process of electroreduction+desalination in a reactor or electrochemical cell or electrosynthesis cell that will be formed by, at least, one cathode and one anode, one catholyte, one anolyte, one dilute and one concentrate, separated by some suitable separating means (A.M. and C.M. of FIG. 2) such as an ionic exchange membrane or any other suitable separator.

Electrodes constituted by graphite, carbon or derivatives thereof, lead, tin, zinc, copper, platinized titanium, any other steel or alloy in which iron, aluminum, or alloys thereof with gallium, indium or thallium, gas diffusion cathodes intervene, or preferably, a three-dimensional electrode of graphite, carbon or derivatives thereof with a suitable current collector can be used as a cathode. A stable electrode selected from among: Ti-Pt, Ti-Pb, DSA oxygen, DSA chlorine, $PbO_2$, vitreous carbon, graphite, a gas diffusion anode, is used as an anode, without these electrodes being restrictive of the invention. However, so that the yields and selectivity are adequate and in order to prevent contamination by heavy metals in the final product, as lead has to be used, it is preferable to use one or several cathodes constituted by a lead electrode, since the nature and shape of the electrode decisively influences the quality of the final product. Likewise, the required pharmaceutical quality implies that the electrosynthesis cell includes one or several anodes constituted by DSA-oxygen, for the purpose of preventing the problems of corrosion detected in other types of anodes used and that would lead to a product of non-pharmaceutical quality (US Pharmacopoeia).

The catholyte and the dilute (FIG. 2) will be fed by the same solution coming from the acetylation of III and that contains IV+acetate. The anolyte and the concentrate may be fed by the same aqueous solution of any saline electrolyte, for example, an aqueous sodium acetate solution (NaAC).

The anolyte and the dilute and the catholyte and the concentrate, respectively, have to be necessarily separated by some suitable separating means, such as an ionic exchange membrane, preferably a selective membrane that permits the passing of anions but not of cations (A.M.) in, or by any other type of separator. These membranes will be selected between the commercial ones—NAFION, NEOSEPTA, SYBRON, LONICS, AQUALYTIC or any other commercial one.

The dilute and the concentrate have to be necessarily separated by some suitable separating means, such as an ionic exchange membrane, preferably a selective membrane that permits the passing of cations but not of anions (CM) in, or by any other type of separator. These membranes will be chosen among the commercial ones—NAFION, NEOSEPTA, SYBRON, LONICS, AQUALYTIC or any other commercial one.

Just as it has been indicated, the electrodes may be flat or may have any other shape or structure, and they may be arranged in a filter-press type cluster or the like. Preferably, three-dimensional electrodes must be used.

The connection of the electrodes to the source may be monopolar, bipolar or mixed, preferably, the bipolar one due to the specific design of the electrosynthesis cell. Electrolysis may be carried out at a temperature between 0 and 90° C.

The current density must be comprised between 1 $mA/cm^2$ and 5000 $mA/cm^2$ and does not have to remain, necessarily, constant during electrolysis.

Once the electrosynthesis is considered to be finished, the catholyte is subjected to a reduced pressure distillation process in which the water is eliminated. Then an alcohol, preferably, one of the following ones: ethanol, isopropanol, methanol, is added to the residue. A hydrochloric acid solution is added to the resulting solution until the pH reaches a value lower than 2. A white precipitate which is separated, will appear. The resulting solution is subjected to reduced pressure distillation until all the solvent is eliminated, remaining a solid which corresponds to the desired product (I). This white solid is crystallized and recrystallized in water obtaining a white solid that complies with the characteristics of the desired product so that it is used as a pharmaceutical product. These analytical characteristics are the same ones as those that were indicated above for the first alternative.

As one can see from what has been stated above, with the process of the present invention, the use of (II) as a starting product is avoided, since cystine (III) or the bis-acetyl-cystine (IV) is started with aside from a separation of N-acetyl-L-cysteine (I) from a solution with a low salt content. All of this results in a simplification of the process and in a separation of the desired product (I) in the best conditions.

On the other hand, two electrochemical techniques (consecutive or simultaneous electrodialysis and electrochemical reduction) which reduce the problems of an environmental impact practically to nothing, with respect to other reduction or desalination techniques, are used. The safety of the electrochemical reduction technique with regard to the use of a conventional reducing agent such as Zn for example must be emphasized.

Besides, the cascade connection between the electrodialysis and electrochemical reduction steps is possible in the event that both steps are consecutive (first alternative), said connection not being necessary when both steps are carried out simultaneously in the same electrochemical reactor.

Therefore, the process of the present invention has clear advantages over those of the prior art, which can be summarized in the following points:

a) It avoids the use of reducing agents (metals).

b) The reduction is done electrochemically.

c) It is not necessary to precipitate and isolate the salts, since they are eliminated by another electrochemical technique: Electrodialysis.

d) Isolation of the reaction intermediate is not required.

e) The conditions of the process help to prevent the formation of undesired impurities.

f) Practically no environmental impact g) Safety in the handling of reagents, since the dangerous ones (zinc) are eliminated, avoiding the uncontrolled release of hydrogen.

h) Reduction of the number of steps of the process i) Totally automatic process j) Better quality of the product, since the specifications of US Pharmacopoeia are complied with.

k) Upon not starting with cysteine, rather unstable in a basic medium, directly with the reduction process the formation of N-acetyl-L-cysteine, much stabler than the cysteine in the medium is achieved, thus avoiding the use of an inert atmosphere and low temperatures.

EMBODIMENTS OF THE INVENTION

Figure 1:
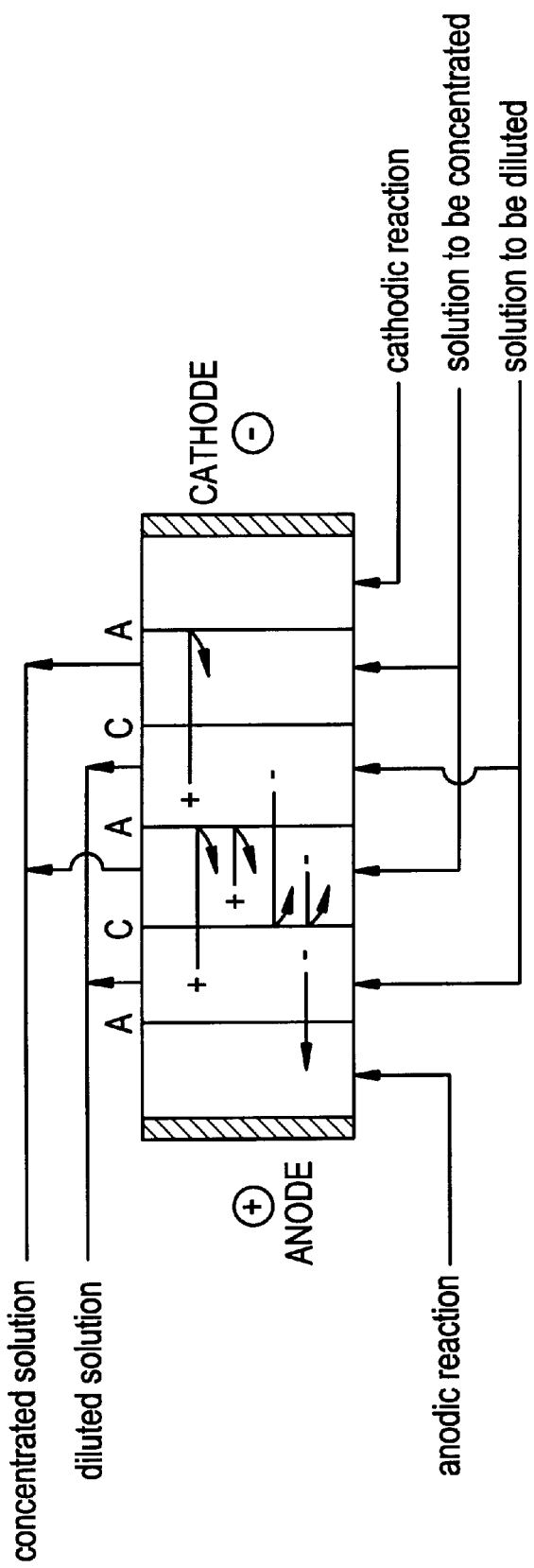
FIG. 1 illustrates the electrochemical device used to carry out the first alternative of the process of the present invention. A represents the anionic membrane and C represents the cationic membrane.
Figure 2:
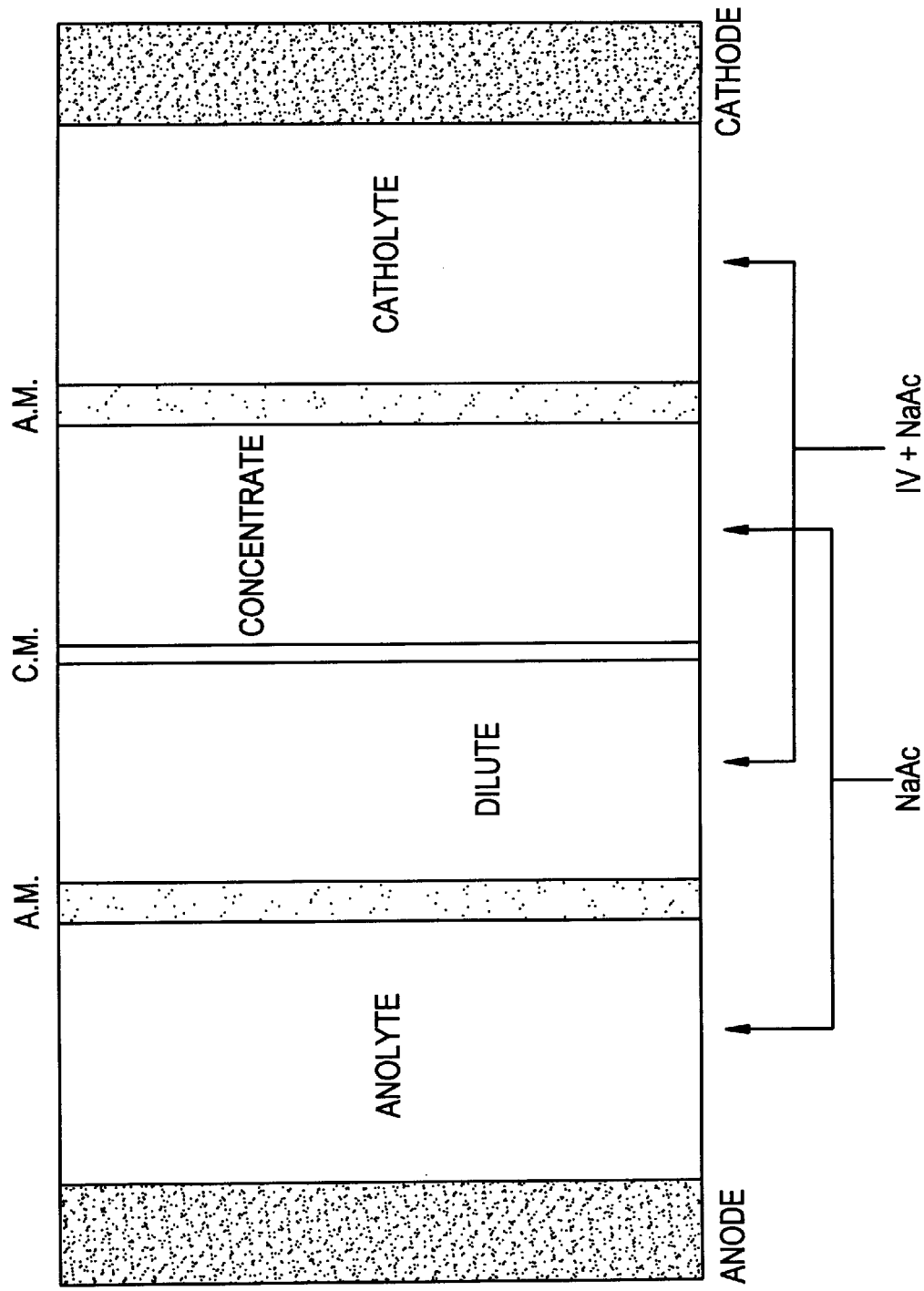
FIG. 2 illustrates the electrochemical device used to carry out the second alternative of the process of the present invention. A.M. represents the anionic membrane and C.M. represents the cationic membrane.

The present invention is additionally illustrated by means of the following Examples which do not aim to be restrictive of its scope defined only and exclusively in the attached claim set.

EXAMPLE 1

1) ACETYLATION OF (III) TO OBTAIN (IV)

24 grams of L-cystine are dissolved in 100 ml. of 2 N NaOH, after cooling the solution to 0° C., 500 ml of cold 2 N NaOH and 50 ml. of acetic anhydride are added alternately in small amounts with vigorous stirring. The pH is maintained the whole time at approximately 9. After completing the addition, 2 hours later 6 N HCl is added up to pH 6–7.

2) ELECTRODIALYSIS OF THE SOLUTION THAT CONTAINS (IV)

For the purpose of eliminating the most part of the salt content, the previously obtained solution is subjected to an electrodialysis process with the following characteristics:

REACTOR: 10 ELECTRODIALYSIS CELLS

CATIONIC MEMBRANE: CMX

ANIONIC MEMBRANE: AMX

CATHODE: STAINLESS STEEL

ANODE: Ti/Pt

CATHOLYTE+ANOLYTE: 2.0 liters of 0.1 M sodium acetate

FLUX: 150 L/H

SOLUTION TO BE DISSOLVED: The solution obtained in the above section (contains IV, sodium acetate and water)

pH: 7.3

FLUX: 300 L/H

SOLUTION TO BE CONCENTRATED: 1.5 liters of 0.1 M sodium acetate solution pH: 7.5

FLUX: 300 L/H

TOTAL CIRCULATED CHARGE: 100% of the total charge to be circulated

CURRENT DENSITY: It varied between 50–250 A/m$^2$

After the electrodialysis has finished, a solution with a pH of 5.3 that has lost most of the initial sodium acetate content is obtained in the diluted solution. This solution will then be subjected to an electroreduction process.

3) ELECTROREDUCTION OF THE SOLUTION THAT CONTAINS (IV) AND THAT COMES FROM THE ELECTRODIALYSIS STEP

The previous solution is subjected to an electroreduction process in an electrochemical reactor of a unit area of 200 cm$^2$, composed of:

CATHODE: Lead/Carbon

ANODE: Dimensionally stable anode

MEMBRANE: NAFION

The catholyte was the solution coming from the previous step and catalogued as diluted solution and with a pH of 5 3. The anolyte was a 4×10$^{-2}$ M sulfuric acid solution. After circulating a charge of 24 A.h maintaining a current density between 25–50 mA/cm$^2$, the catholyte solution is placed in a rotary evaporator eliminating the water at reduced pressure. Then the residue is dissolved in methanol and the pH is adjusted with hydrochloric acid up to a value lower than 2. A white precipitate that is filtered appears; the filtrate is subjected to reduced pressure distillation appearing a crystalline solid that is recrystallized in water, giving rise to a white solid that is identified as N-acetyl-cysteine (90%).

EXAMPLE 2

1) ACETYLATION OF (III) TO OBTAIN (IV)

24 grams of L-cystine are dissolved in 100 ml of 2 N NaOH, after cooling the solution to 0° C., 500 ml of cold 2 N NaOH and 50 ml of acetic anhydride are added alternately and in small amounts with vigorous stirring. The pH is maintained the whole time at approximately 9. After completing the addition, 2 hours later 6 N HCl is added up to a pH 6–7.

2) SIMULTANEOUS ELECTROREDUCTION+DESALINATION OF THE SOLUTION THAT CONTAINS (IV)+SODIUM ACETATE (NaAc)

The solution coming from the previous section is fed as a catholyte+dilute, for the purpose of converting IV into I and in turn to eliminate most of the salt content (sodium acetate). This reactor has the following characteristics:

REACTOR: 1 BASIC UNIT WITH FOUR COMPARTMENTS OF 63 $cm^2$ OF UNIT AREA PER COMPARTMENT
CATIONIC MEMBRANE: N117
ANIONIC MEMBRANE: ACS
CATHODE: LEAD/CARBON
ANODE: DIMENSIONALLY STABLE ANODE
ANOLYTE+CONCENTRATE: 0.75 liters of 0.1 M sodium acetate
CATHOLYTE+DILUTE: 0.35 liters of the solution obtained in the previous section (contains IV, sodium acetate and water)
pH: 7.3
TOTAL CIRCULATED CHARGE: 100% of the total charge to be circulated
CURRENT DENSITY: It varied between 50–250 $A/m^2$ After finishing electrodialysis, a solution with a pH of 5.3 that has lost most of the initial sodium acetate content is obtained in the catholyte+dilute compartment and in which IV has been reduced to I. This solution is placed in a rotary evaporator eliminating the water at reduced pressure. Then the residue is dissolved in methanol and the pH is adjusted with hydrochloric acid up to a value lower than 2. A white precipitate that is filtered appears; the filtrate is subjected to reduced pressure distillation appearing a crystalline solid that is recrystallized in water, giving rise to a white solid that is identified as N-acetyl-cysteine (90%)

What is claimed is:

1. A process for electrochemical synthesis of N-acetyl-cysteine from cystine, the process comprising the steps of
   (A) preparing N-acetyl-cysteine from L-cystine, by
      (i) acetylation of L-cystine to produce N-acetyl-cystine;
      (ii) electroreduction and desalination by electrodialysis of the N-acetyl-cystine thus produced to give N-acetyl-cysteine; or
   (B) preparing N-acetyl-cysteine from L-cystine, by
      (i) acetylation and desalination by electrodialysis of L-cystine to produce N-acetyl-cystine; or
      (ii) electroreduction of N-acetyl-cystine, to produce N-acetyl-cysteine;
   (C) preparing N-acetyl-cysteine from L-cystine, by means of the following steps:
      (i) electroreduction of L-cystine to produce L-cysteine;
      (ii) acetylation and desalination by electrodialysis of L-cysteine to produce N-acetyl-cysteine.

2. A process according to claim 1, wherein the electroreduction and desalination in step (A)(ii) is carried out in the same reactor or electrochemical cell formed by, at least, one cathode, one anode and separating means.

3. A process according to claim 2, wherein the cathode is selected from the group constituted by graphite, carbon, lead, tin, zinc, copper, platinized titanium, any steel or iron alloy, aluminum or alloys thereof with gallium, indium or thallium electrodes, and gas diffusion cathodes.

4. A process according to claim 2, wherein the anode is comprised of a stable electrode selected from the group consisting of Ti-Pt, Ti-Pb, DSA oxygen, DSA chlorine, $PbO_2$, vitreous carbons, graphite, gas diffusion anodes.

5. A process according to claim 2, wherein the separating means are constituted by ionic exchange membranes.

6. A process according to claim 2, wherein an electrolytic process is carried out at a temperature between 0 and 90° C. and at a current density between 1 $mA/cm^2$ and 5000 $mA/cm^2$, the density being constant or variable during the course of the process.

7. A process according to claim 1, wherein the desalination operations in step (B)(i) and step (C)(ii) are carried out in an electrochemical cell constituted by, at least, one cathode, one anode and separating means.

8. A process according to claim 7, wherein the cathode is constituted by a flat or three-dimensional cathodes selected from the group consisting of metal, conductor oxide, carbonous compound or graphite derivative electrode and gas diffusion cathodes.

9. A process according to claim 7, wherein the anode is constituted by a stable electrode selected from the group consisting of Ti-Pt, Ti-Pb, DSA oxygen, DSA chlorine, $PbO_2$, vitreous carbons, vitreous graphite or carbonous derivatives, gas diffusion anode.

10. A process according to claim 7, wherein the separating means are selected from anionic and cationic membranes.

11. A process according to claim 7, wherein an electrolytic process is carried out at a current density between 1 and 1000 $mA/cm^2$, the density being constant or variable during the course of the process.

12. A process according to claim 1, wherein the electroreduction operations in step (B)(ii) and step (C)(i) are carried out in an electrolytic cell constituted by, at least, one cathode, one anode and separating means.

13. A process according to claim 12, wherein the cathode is constituted by an electrode selected from the group consisting of graphite, carbon, lead, tin, zinc, copper, platinized titanium, any steel or alloy in which iron aluminum or alloys thereof with gallium, indium or thallium intervene, and gas diffusion cathodes.

14. A process according to claim 12, wherein the anode is constituted by a stable electrode selected from the group consisting of Ti-Pt, Ti-Pb, DSA oxygen, DSA chlorine, $PbO_2$, vitreous carbons, vitreous graphite or carbonous derivatives, graphite, and gas diffusion anodes.

15. A process according to claim 12, wherein the separating means are constituted by ionic exchange membranes.

16. A process according to claim 12, wherein an electrolytic reduction process is carried out at a temperature between 0 and 90° C. and at a current density between 1 $mA/cm^2$ and 5000 $mA/cm^2$, the density being constant or variable during the process.

17. A process according to claim 1, wherein steps (B)(i) and (ii) are carried out independently or successively.

18. A process according to claim 1, wherein steps (C)(i) and (ii) are carried out independently or successively.

19. A process according to claim 1, wherein in the electrodialysis there is a solution to be diluted that has a concentration of alkali metal or alkaline earth metal acetate between 0.01 M and a maximum concentration that permits its solubility in the medium in which it is dissolved.

20. A process according to claim 19, wherein the acetate is sodium acetate.

21. A process according to claim 1, wherein in the electrodialysis, the N-acetyl-cysteine is used as the solution to be diluted, in a concentration of 0.01 and 4 M.

22. A process according to claim 21, wherein the solution in electrodialysis has a pH between 2.5 and 10.

23. A process according to claim 1, wherein in the electrodialysis a solution to be concentrated that is a salt solution, is used.

24. A process according to claim 23, wherein the salt is an alkali metal or alkaline earth metal acetate.

25. A process according to claim 24, wherein the acetate is sodium acetate.

26. A process according to claim 23, wherein the solution to be concentrated has a concentration between 0.01 M and a maximum concentration that permits solubility of the salt in the medium in which it is dissolved.

27. A process according to claim 23, wherein in the electroreduction intervenes a catholyte constituted by a solution that has a concentration of alkali metal or alkaline earth metal acetate concentration between 0.01 M and a maximum concentration that permits solubility of the salt in the medium in which it is dissolved.

28. A process according to claim 23, wherein the acetate is sodium acetate.

29. A process according to any of claims 20, 25 or 28, wherein the sodium acetate is present in a concentration between 0.01 and 20 M.

30. A process according to claim 1, wherein the catholyte in the electroreduction has a pH between 2.5 and 10.

31. A process according to claim 1, wherein in the electroreduction a saline electrolyte is used as an anolyte.

32. A process according to claim 1, wherein in the electroreduction a catholyte that has a concentration of N-acetyl-cysteine between 0.01 and 4 M is used.

* * * * *